(12) United States Patent
Miyahara et al.

(10) Patent No.: US 6,457,349 B1
(45) Date of Patent: Oct. 1, 2002

(54) METHOD OF TESTING HARDNESS OF MICRO REGION

(75) Inventors: Kensuke Miyahara; Saburo Matsuoka; Nobuo Nagashima, all of Ibaraki (JP)

(73) Assignee: Japan as represented by Director General of National Research Institute for Metals, Ibaraki (JP)

( * ) Notice: Subject to any disclaimer, the term of this patent is extended or adjusted under 35 U.S.C. 154(b) by 0 days.

(21) Appl. No.: 09/647,099

(22) PCT Filed: Mar. 26, 1999

(86) PCT No.: PCT/JP99/01565

§ 371 (c)(1),
(2), (4) Date: Nov. 20, 2000

(87) PCT Pub. No.: WO99/50640

PCT Pub. Date: Oct. 7, 1999

(30) Foreign Application Priority Data

Mar. 26, 1998 (JP) ............................... 10-078169

(51) Int. Cl.$^7$ ................................................. G02N 3/30
(52) U.S. Cl. ................................................. 73/82; 73/78
(58) Field of Search ............................ 73/12.01, 78, 82

(56) References Cited

U.S. PATENT DOCUMENTS

| | | | | |
|---|---|---|---|---|
| 4,036,048 A | * | 7/1977 | Webster | 73/81 |
| 4,059,990 A | * | 11/1977 | Glover et al. | 73/81 |
| 4,304,123 A | * | 12/1981 | Aschinger | 73/81 |
| 5,804,707 A | * | 9/1998 | Scarton et al. | 73/82 |
| 6,155,104 A | * | 12/2000 | Suresh et al. | 73/81 |

FOREIGN PATENT DOCUMENTS

| | | |
|---|---|---|
| JP | 5-281119 | 10/1993 |
| JP | 8-159941 | 6/1996 |

* cited by examiner

*Primary Examiner*—Hezron Williams
*Assistant Examiner*—Katina Wilson
(74) *Attorney, Agent, or Firm*—Wenderoth, Lind & Ponack, L.L.P.

(57) ABSTRACT

A testing method is provided for determining the hardness of a micro region, using indentation curves indicating relations between observed penetration depths and indenting forces when an arbitrary shaped indenter is pushed into standard samples of plural types. The method involves (1) measuring relations between observed penetration depths and indenting forces when the arbitrary shaped indenter is pushed into standard samples of plural types, to prepare the indentation curves, (2) determining a reference function indicative of macro hardness, by standardizing the relations between the indenting forces and macro hardness at the same penetration depth as an index, for the indentation curves of the standard samples of plural types, (3) measuring a relation between the penetration depth and indenting force of an arbitrary sample, and (4) determining the hardness of a micro region from the measured value in step (3) according to the reference function as determined in step (2).

10 Claims, 16 Drawing Sheets

HM40H.PRM

AFM image after the test for $SiO_2$ type inclusions in valve spring steels

INCL4.PRM

INCL4H.PRM

METHOD OF TESTING HARDNESS OF MICRO REGION

This application is a 371 of PCT/JP99/01565 filed Mar. 26, 1999.

TECHNICAL FIELD

This invention concerns a method of testing hardness of a micro region. More specifically, it relates to a novel method of testing hardness capable of accurately evaluating the hardness of a micro region such as a nanometer region that can not be measured by a test for macro hardness such as Vickers hardness.

BACKGROUND ART

Heretofore, in a Vickers hardness test which is typical for the macro hardness test, the hardness has been determined in accordance with a definition of dividing an indenting force with an area of contact. Since there is no substantial size effect in the macro hardness, the indenting force with force employed is usually properly selected.

On the contrary, in the hardness test for a micro region such as a nanometer region, when the hardness is calculated in accordance with the definition based on a measured indenting force and a penetration depth as usual, it results in a problem that an apparent hardness increases since the size effect is not negligible. Then, it is necessary to eliminate the influence of the size effect. In the existent method, a correlation is determined between a hardness determined at a certain penetration depth in accordance with the definition and a macro hardness, or an indentation curve is approximated by a certain function and a correlation between the parameter and the hardness is determined.

However, the existent study for the correlation with the macro hardness is scarcely considered effective. For an arbitrary sample, the hardness of a micro region can not accurately be evaluated at present.

On the other hand, evaluation for the hardness of the micro region has provided an extremely important subject for the research and development of new metal materials and semiconductors.

In view of the above, it is a subject of the invention in the application to overcome the limit of the prior art as described above in indenting an indenter into a sample and evaluating the hardness of a material based on a relation between an indenting force and a penetration depth, and provide a novel method eliminating the influence of the size effect that the apparent hardness increases in the test for the hardness of a micro region with the penetration depth or an indent depth of 1 μm or less, considering the micro hardness in the micro hardness test in the same manner as in the macro hardness in the Vickers hardness test, and capable of effectively utilizing the existent knowledge for the macro hardness and accurately evaluating the hardness of a nanometer region.

SUBJECT OF THE INVENTION

The invention of the application, for solving the foregoing subject, provides a testing method for determining the hardness of a micro region, into which an indenter is pushed, from an indentation curve indicating a relation between a penetration depth observed when an indenter in an arbitrary shape is pushed in and an indenting force, characterized by comprising (1) measuring, in addition to macro hardnesses, relations between penetration depths observed when an indenter in an arbitrary shape is pushed in and indenting forces, for a plurality types of standard samples, (2) determining a reference function indicating a macro hardness by standardizing a relation between an indenting force and a macro hardness with the same penetration depth used as an index, for indentation curves of a plurality types of standard samples indicating relations between penetration depths and indenting forces, (3) measuring relations between penetration depths and indenting forces for arbitrary samples, and (4) determining the hardness of a micro region from the measured values according to the reference function.

Further, according to the invention of this application, a plurality of standard samples having identical mechanical properties in the micrometer region and the nanometer region are used in the method described above.

BEST MODE FOR PRACTICING THE INVENTION

The invention of the application has the features as described above and embodiments will be explained.

In this invention, the correlation with the result of a macro hardness test such as by a Vickers test or a Knoop test is considered with a new point of view. Then, for the hardness test of a micro region, indenters of arbitrary shape are used, and a relation between the penetration depth and the indenting force by the indenter is noted in this invention.

For indentation of the indenter, a cantilever system or double lever system and various other types of systems, as well as apparatus therefor may be used.

Then, examples are shown below and the test method according to this invention is to be explained with reference to the examples.

EXAMPLE

At first, in the method of this invention, as a first step of a test method for determining the hardness of a micro region into which an indenter is pushed, from an indentation curve indicating a relation between a penetration depth observed when an indenter in an arbitrary shape is pushed in and an indenting force, (1) relations between penetration depths observed when an indenter in an arbitrary shape is pushed in and indenting forces are measured for a plurality types of standard samples as described above.

The standard samples may be in any combination of a plurality of species such as iron, nickel and molybdenum. However, it is appropriate that each of the standard samples has an identical mechanical properties in the macro meter region and the nanometer region.

Further, for the standard samples, single structure materials or composite phase fine structure materials are selected. It is not preferred that the materials have a layer different in the mechanical properties such as a surface treated layer.

In the examples, single crystals of tungsten, molybdenum, nickel and iron were used as the single phase material for the standard samples.

For removing the surface treated layer, the surfaces of the samples were electrolytically polished. A micro Vickers test and a micro hardness test by indentation of indenters were conducted for each of the samples. Data from the micro hardness test were obtained by a micro hardness test method based on an inter-atomic force microscope (AFM). For the indenters, two types of diamond triangular pyramidal indenters with an apex of 60° and 115° were used.

Figure 1:
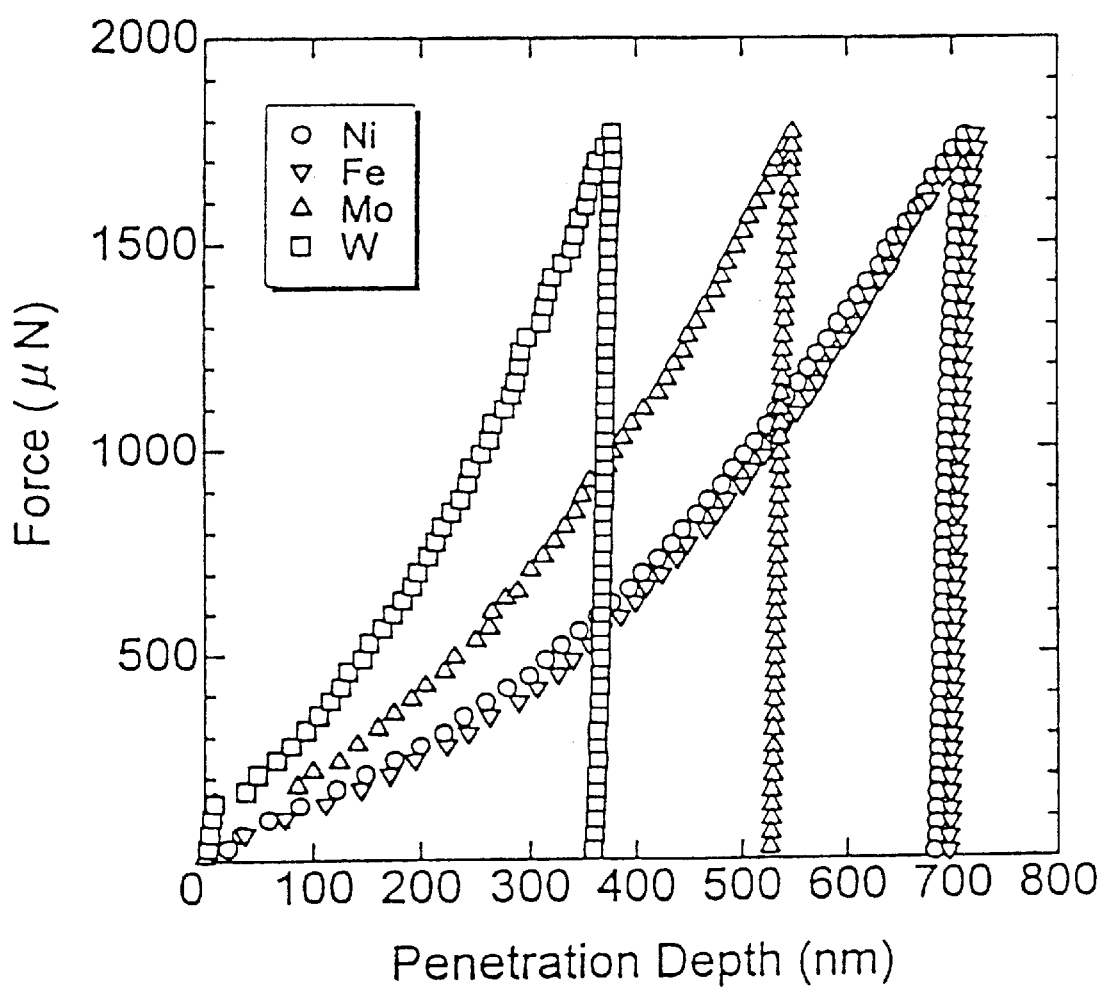
FIG. 1 is a graph illustrating indentation curves on electrolytically polished surfaces for each of metal single crystals (60° indenter)
Figure 2:
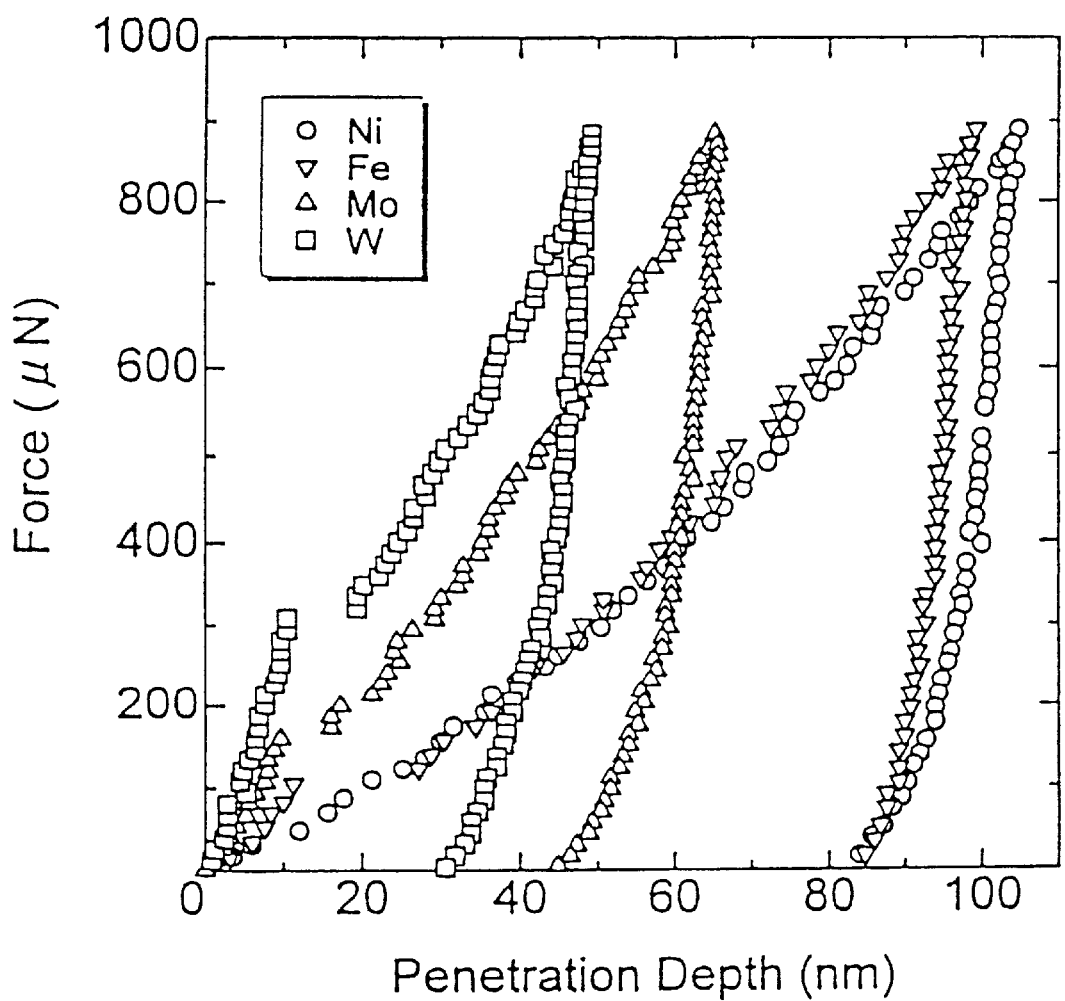
FIG. 2 is a graph illustrating indentation curves on the electrolytically polished surfaces for each of metal single crystals (115° indenter)

FIG. 1 and FIG. 2 are indentation curves indicating relations between penetration depth (nm) by a 60° indenter and a 115° indenter respectively and indenting forces: $F(\mu N)$ for each of the standard samples.

Then as described above, in this invention, as the next step:

(2) a reference function indicating a macro hardness is determined by standardizing a relation between an indenting force and a macro hardness with the same penetration depth used as an index is determined for indentation curves of a plurality types of standard samples indicating relations between penetration depths and indenting forces.

Figure 3:
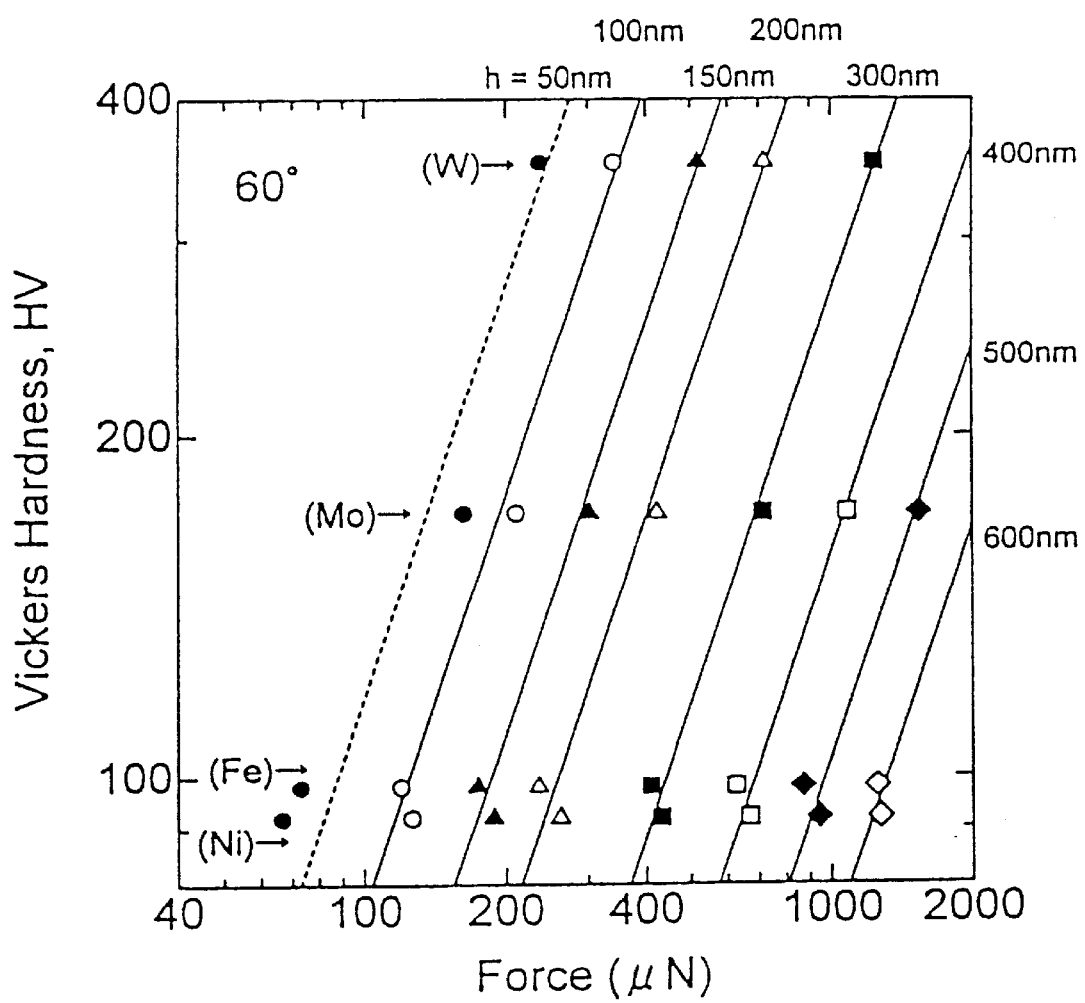
FIG. 3 is a graph illustrating relations between indenting forces and Vickers hardness (60° indenter)
Figure 4:
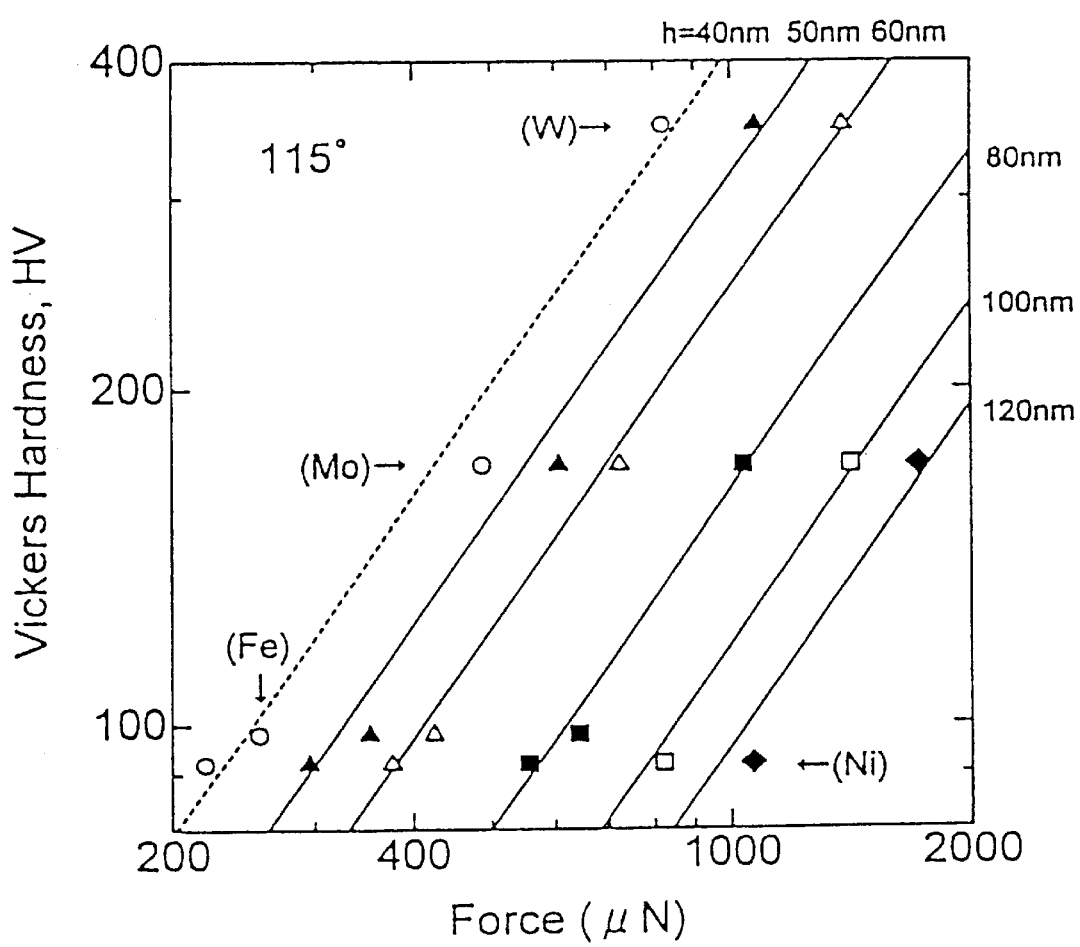
FIG. 4 is a graph illustrating relations between indenting forces and Vickers hardness (115° indenter)

That is, specifically, when a relation between the indenting force F ($\mu$N) and the Vickers hardness HV required for giving a certain penetration depth h (nm) is determined at first from the indentation curves shown in FIG. 1 and FIG. 2, results in FIG. 3 and FIG. 4 are obtained. The relation between the indenting force: F and the Vickers hardness: HV gives straight lines each of an identical gradient in a both logarithmic graph at a penetration depth of 100 nm or more for the 60° indenter in FIG. 3 and at a penetration depth of 500 nm or more for the 115° indenter in FIG. 4. They are represented by the following equations.

$$HV = a \cdot F^n \quad (1)$$

$$n = 1.214 (60° \text{ indenter}) \quad (2)$$

$$n = 1.023 (115° \text{ indenter}) \quad (3)$$

in which a represents a coefficient.

The foregoing indicate that indentation curves for different samples can be standardized as $F/HV^{(t/n)}$.

Figure 5:
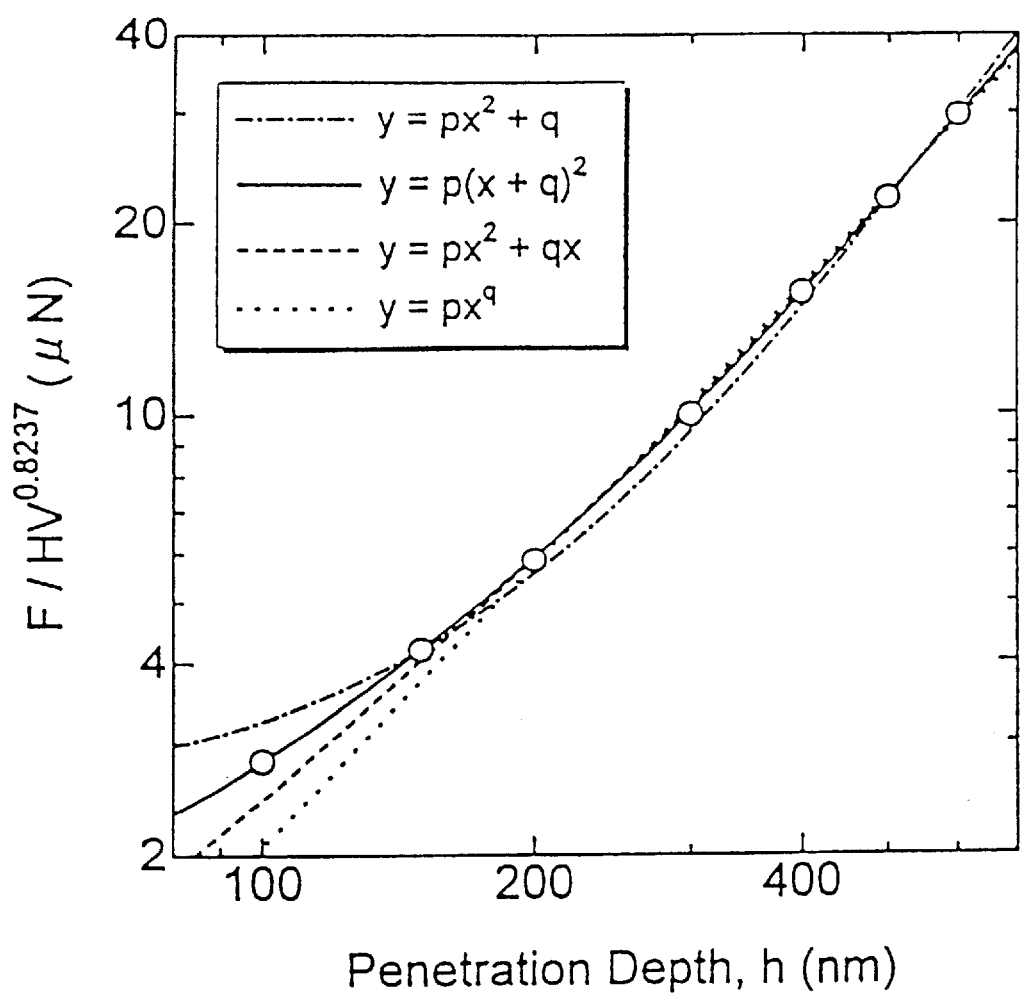
FIG. 5 is a graph illustrating a relation between a standardized indenting force and a penetration depth (60° indenter).
Figure 6:
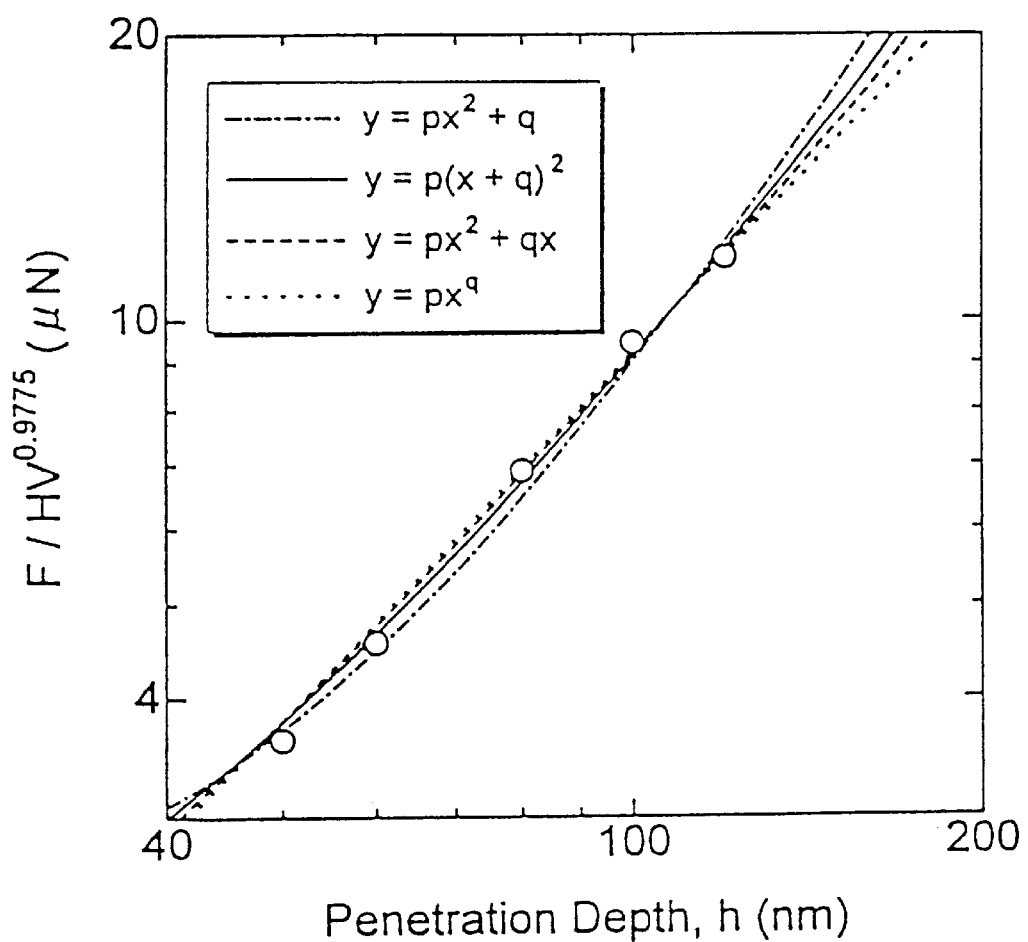
FIG. 6 is a graph illustrating a relation between a standardized indenting force and a penetration depth (115° indenter).

FIG. 5 and FIG. 6 show the relations between $F/HV^{(t/n)}$ and the penetration depth: h. As a result of trying various functions, good approximation can be obtained by the following functions for the case of the 60° indenter and 115° indenter respectively in the examples.

$$F/HV^{(t/n)} = 5.6634 \times 10^{-5} (h + 122.83)^2 \ldots 60° \text{ indenter} \quad (4)$$

$$F/HV^{(t/n)} = 4.6248 \times 10^{-4} (h + 40.468)^2 \ldots 115° \text{ indenter} \quad (5)$$

When rewritten, the Vickers hardness: HV is finally represented as a relation between the penetration depth: h (nm) and the indenting force: F ($\mu$N) by the following reference functions.

$$F/HV^{(t/n)} = [F/\{5.6634 \times 10^{-5} (h + 122.83)^2\}]^{1.214} \ldots 60° \text{ indenter} \quad (6)$$

$$F/HV^{(t/n)} = [F/\{4.6248 \times 10^{-4} (h + 40.468)^2\}]^{1.023} \ldots 115° \text{ indenter} \quad (7)$$

Then, as the final step, in this invention, (3) the relations between the penetration depth and the indenting force are measured for arbitrary samples and
(4) the hardness of a micro region is determined from the measured values according to the reference function.

For instance, the hardness is determined also as the evaluation for the influence of the surface layer as below.

Figure 7:
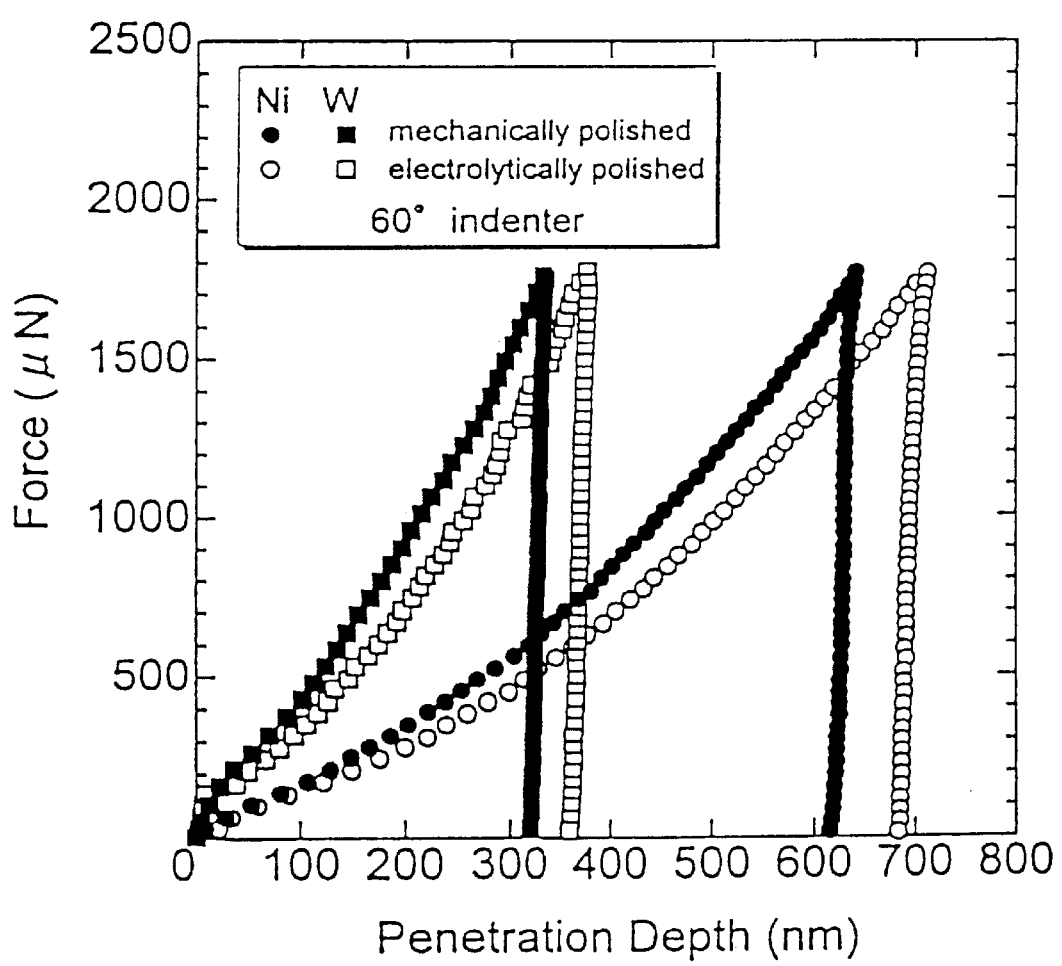
FIG. 7 is a graph illustrating indentation curves for buff polished surfaces and electrolytically polished surfaces for nickel and tungsten (60° indenter)
Figure 8:
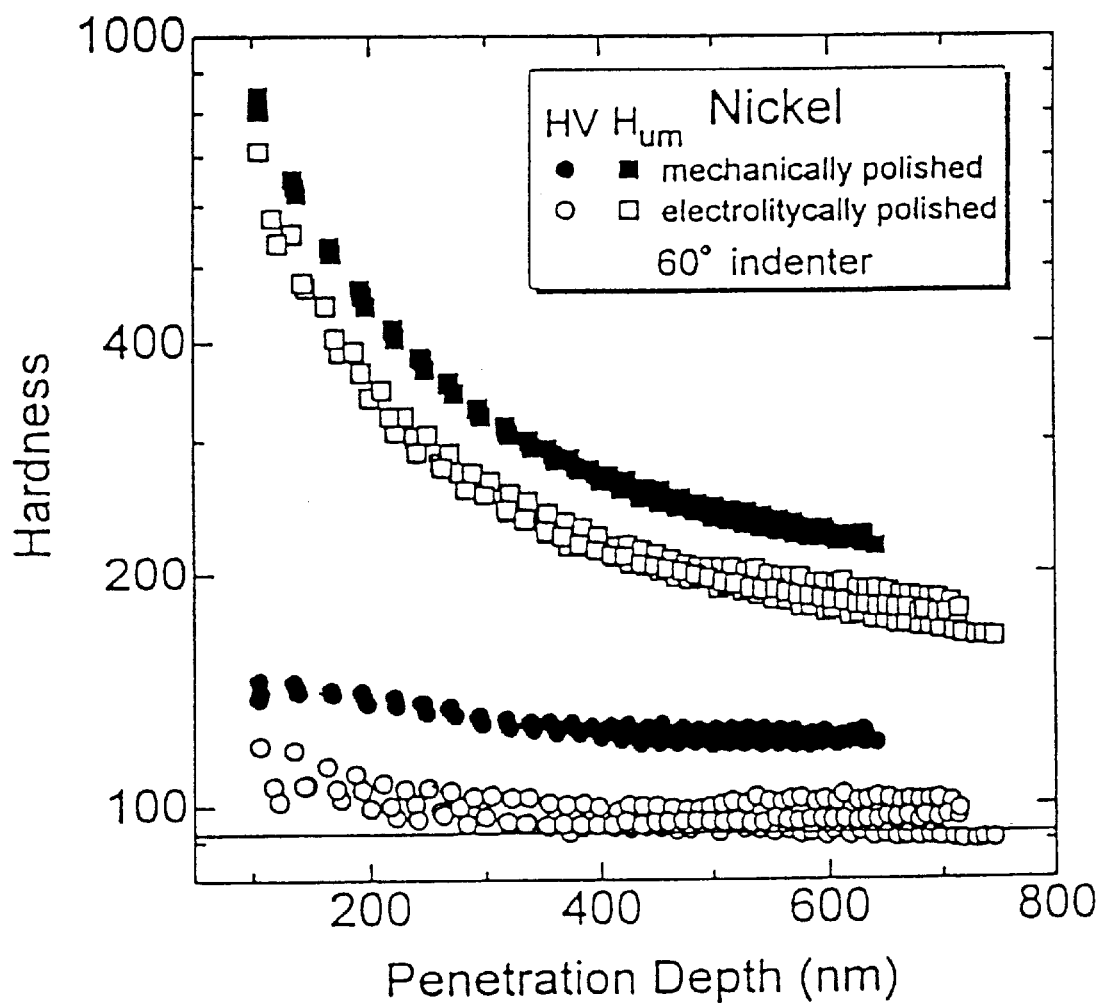
FIG. 8 is a graph illustrating relation between the hardness of nickel and penetration depth.
Figure 9:
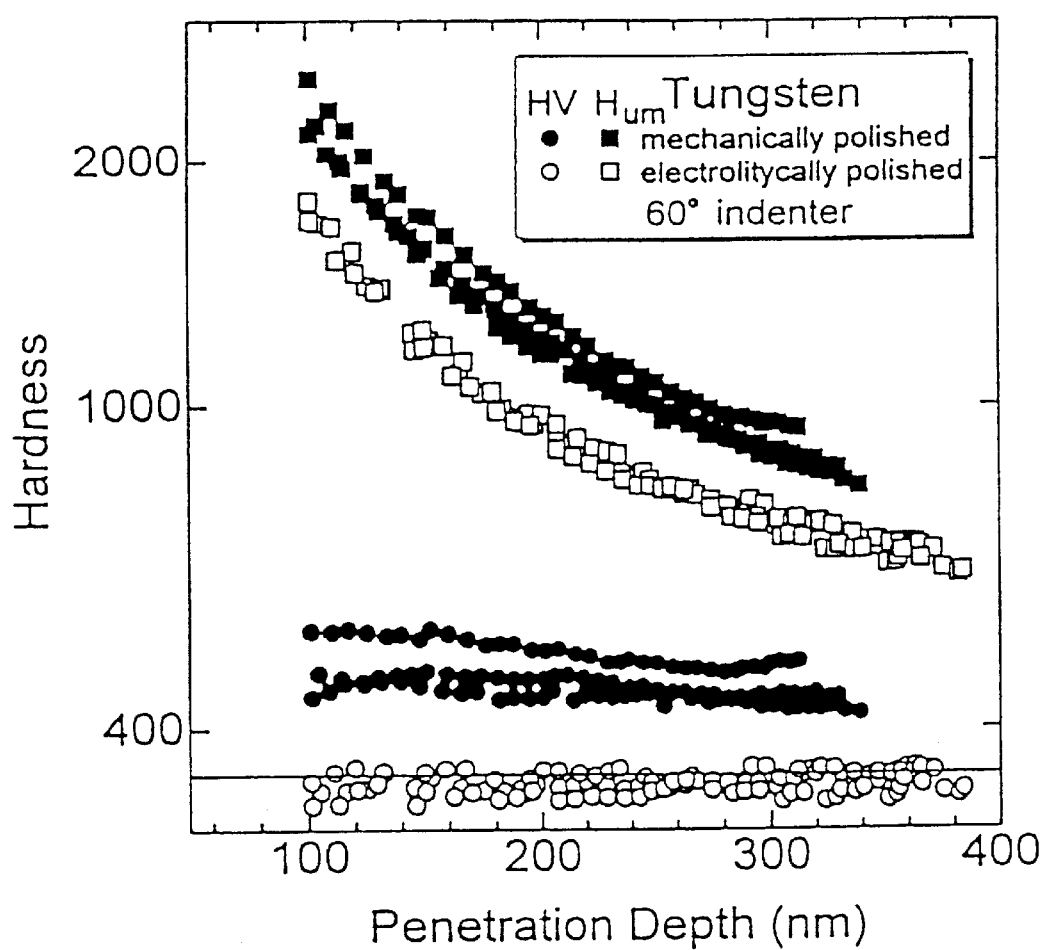
FIG. 9 is a graph illustrating relation between the hardness of tungsten and penetration depth.

That is, for examining the influence of the surface layer, a ultra-micro hardness test on the polished surface of nickel and tungsten single crystals was conducted by using a 60° indenter. FIG. 7 shows indentation curves. Then, the hardness was determined by applying the reference function of the equation (6) to the result of FIG. 7. As a result in accordance with the reference function, FIG. 8 shows the Vickers hardness: HV in the case of nickel and FIG. 9 shows the Vickers hardness: HV in the case of tungsten. For the reference, a hardness: Hum determined by dividing the indentation force with an area of contact in accordance with the ordinary definition is also shown. While the hardness Hum in accordance with the existent definition shows a size effect that the hardness value increases as the penetration depth decreases, such influence of the size effect does not appear in the hardness calculated in accordance with the reference function of the equation (6). The hardness of the buff polished surface is greater than that on the electrolytically polished surface, which is considered to be the effect of the surface treated layer. In view of the above, it can be said that the buff polished surface having not uniform mechanical properties relative to the direction of the depth is not appropriate as the standard sample.

Figure 10:
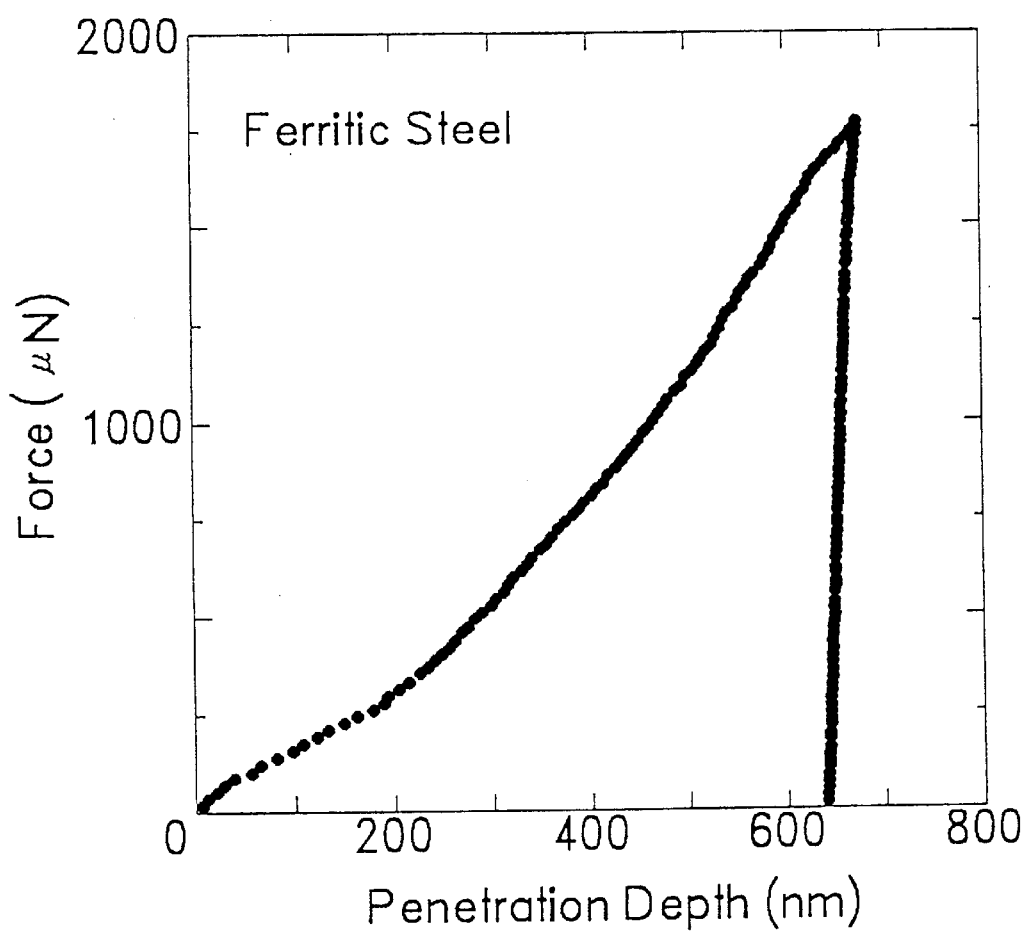
FIG. 10 is a graph illustrating an indentation curve for ferritic steel (60° indenter)
Figure 11:
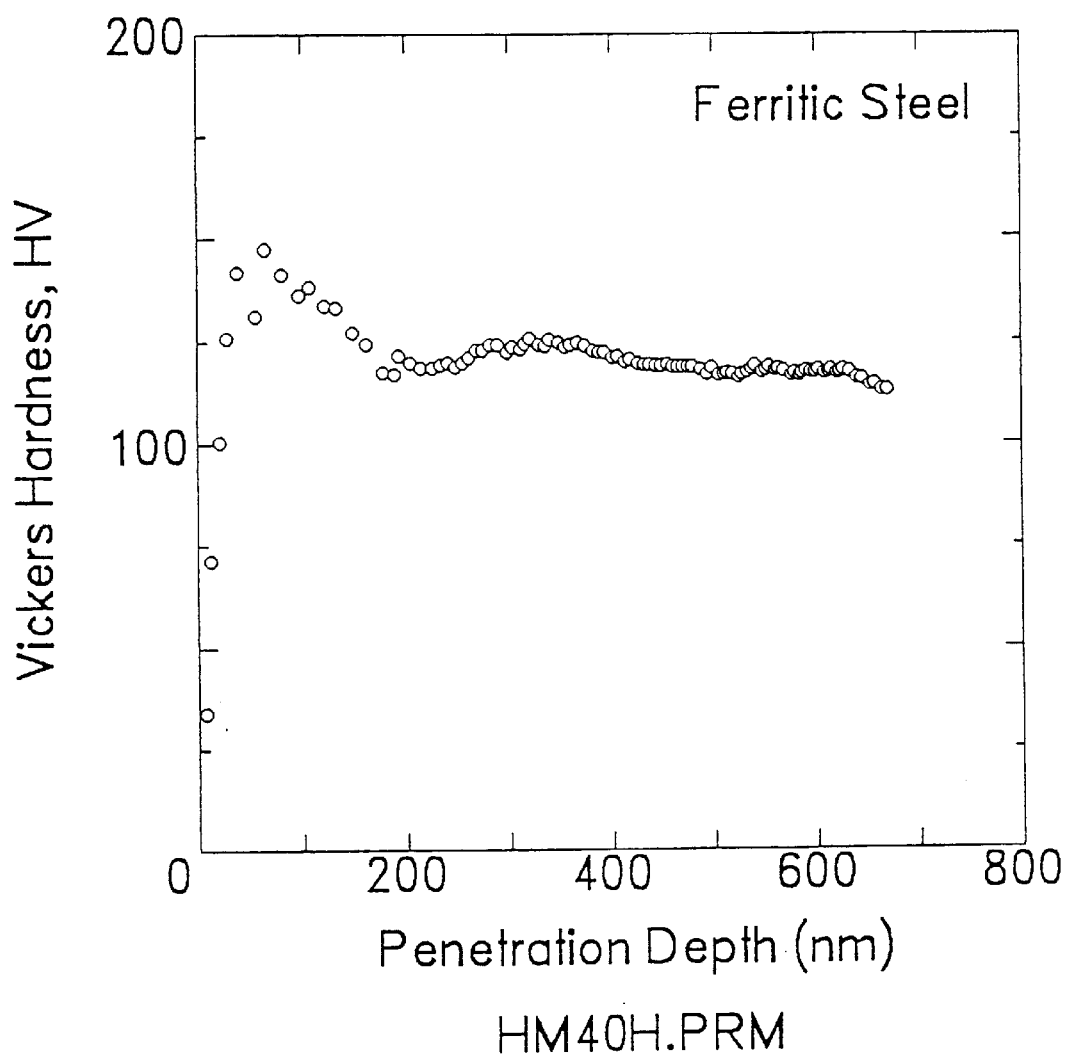
FIG. 11 is a graph illustrating a hardness of ferritic steel.

Further, FIG. 10 is an indentation curve for ferritic steels obtained by using the same 60° indenter. FIG. 11 shows the hardness: HV calculated by using the reference function of the equation (6) from FIG. 10. The hardness in the region free from the influence of the size effect is about 110 to 120, which shows a value approximate to hardness 111 by the Vickers hardness to make it clear that the method of this invention is practically useful. Hardness in both of the cases is identical in this case because the crystal grain size of the ferritic steel is as large as about 50 $\mu$m and the crystal grain boundary gives no substantial effect on the macro hardness. Naturally, since the micro harness is measured in the grains, it is quite free from the effect of the grain boundary.

Figure 12:
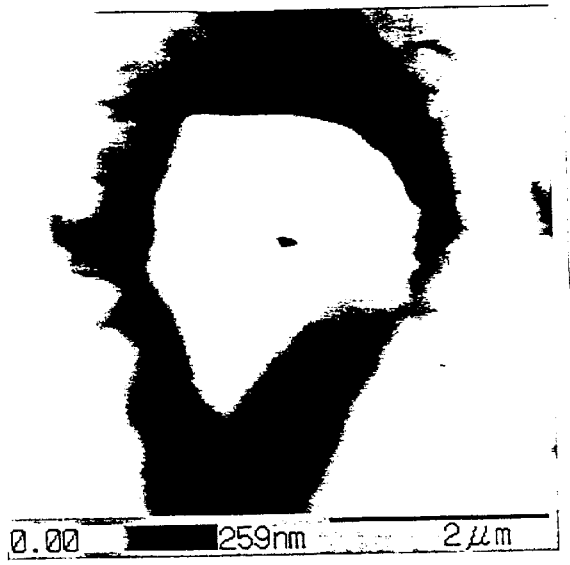
FIG. 12 is an AFM image diagram obtained after conducting an indenting test on inclusions.
Figure 13:
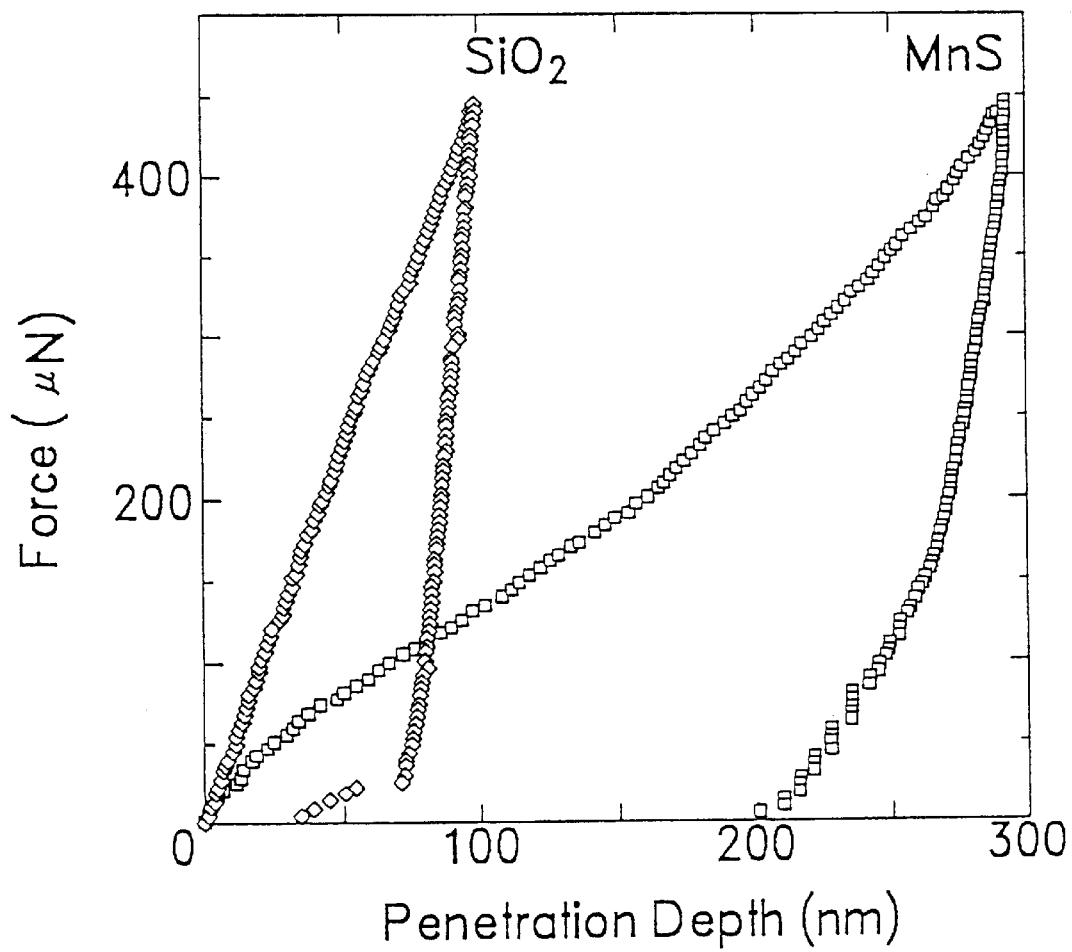
FIG. 13 is a graph showing indentation curves for inclusions (60° indenter)
Figure 14:
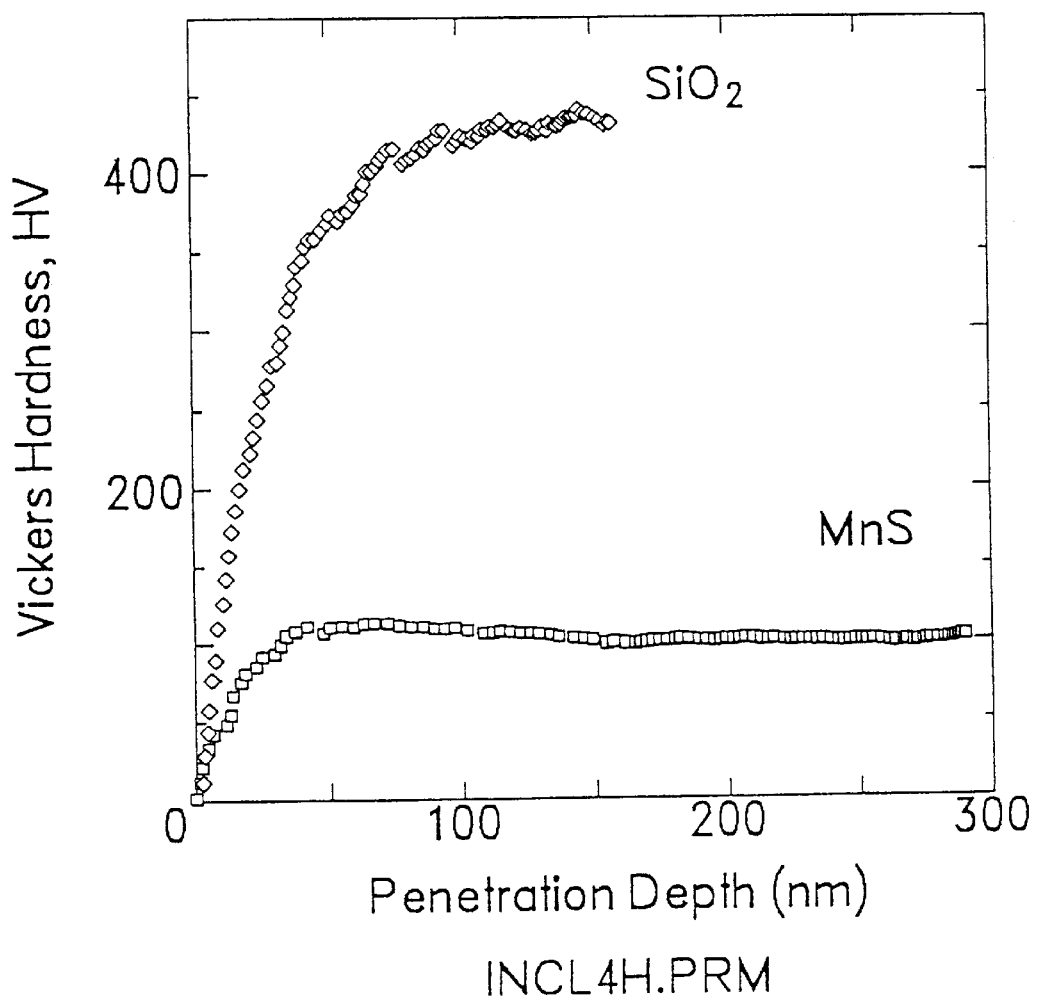
FIG. 14 is a graph illustrating the hardness of inclusions.

As a further test, a ultra-micro hardness test for inclusions contained in the steels was conducted. FIG. 12 shows an AFM image after the test of $SiO_2$ type inclusions. The composition of the inclusions is previously analyzed by EDX. Indentation curves for each of $SiO_2$ type and MnS type inclusions are as shown in FIG. 13 respectively. When the hardness is calculated from respective penetration depths in accordance with the reference function of the equation (6), they are as shown in FIG. 14, in which the hardness is 100 for MnS and the hardness is 430 for $SiO_2$. As described above, it has been found according to this invention that the hardness of inclusions with a diameter of several $\mu m$ can be evaluated.

Figure 15:
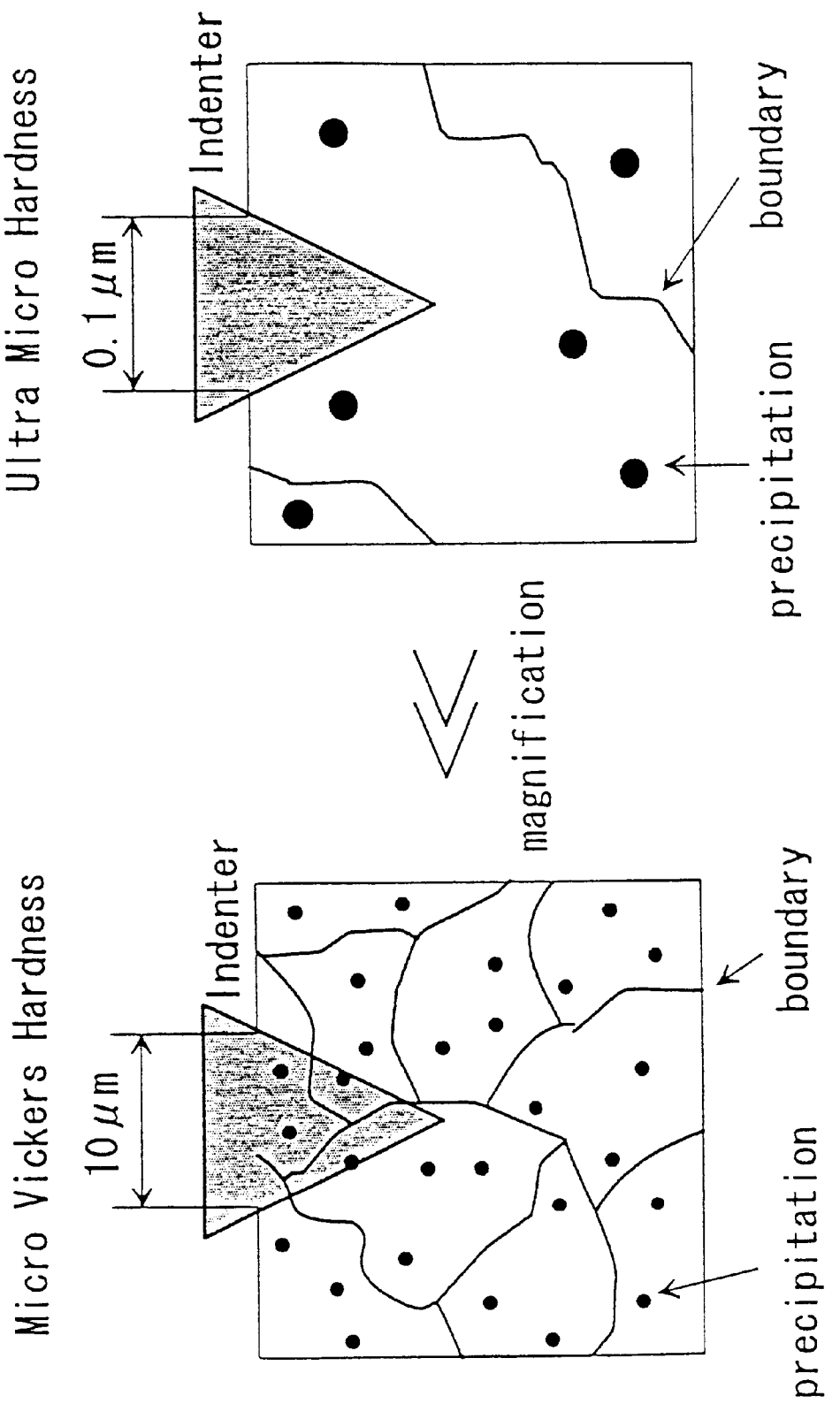
FIG. 15 is schematic views in the hardness test for a composite phase samples and a single phase samples.
Figure 16:
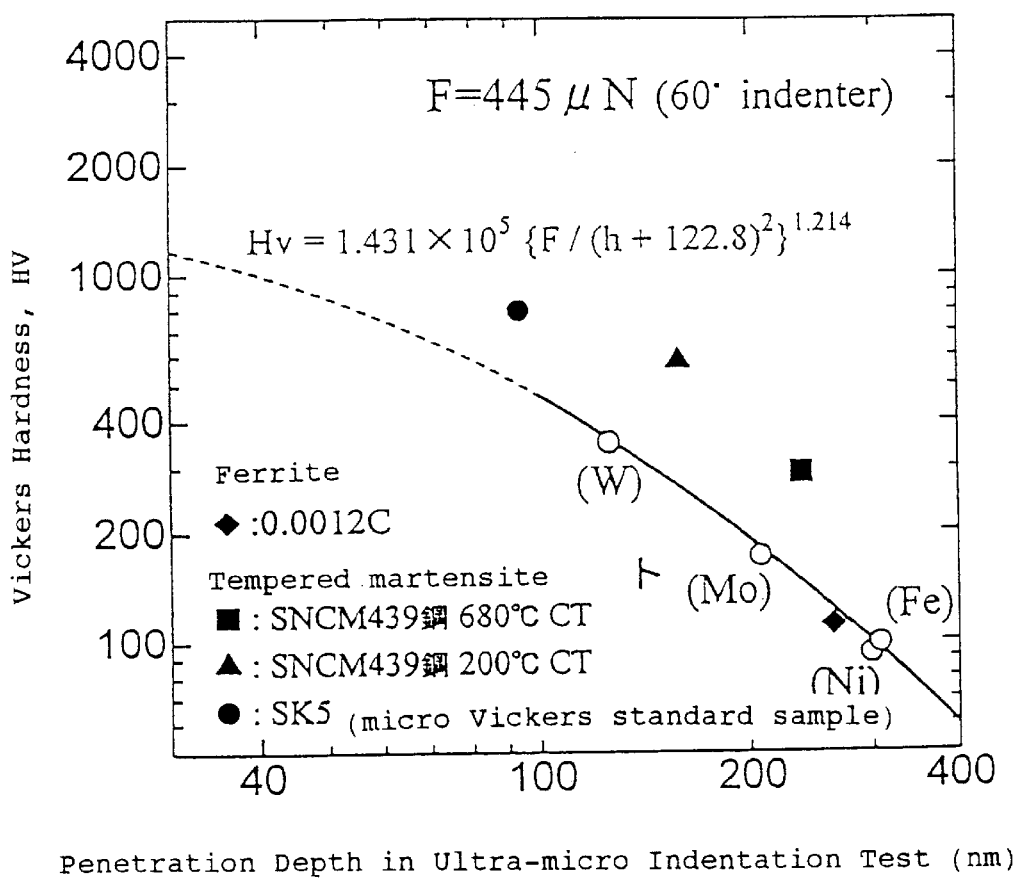
FIG. 16 is a comparative graph between the hardness by a Vickers hardness test and the hardness by an ultra-micro hardness test.

Referring further to the standard samples, composite phase materials such as iron and steel materials have often been used as standard samples for the existent macro hardness test. In a case where the hardness in the macro test is related with the indentation curve in the ultra-macro region in this invention, it is preconditions that the material has identical mechanical properties in both of the tests. FIG. 15 is schematic views in a case of testing the composite phase material by a macro hardness test and a ultra-micro hardness test. The composite phase material is reinforced with crystal grain boundary or precipitates and, when the distance of dispersion between them is several $\mu m$ or more, their effects appear in the macro test but do not appear in the ultra-macro hardness test. Accordingly, they are not appropriate as the standard sample. On the contrary, since it is considered that the characteristics of the single structure material are identical irrespective of the size of the tested region, this appropriate as the standard sample. Also in the case of the composite phase material, since it is considered that the mechanical properties are identical between the macro hardness test and the ultra-micro hardness test for the fine composite phase material in which the distance of dispersion in the strengthening mechanism is at a nanometer order, this material is appropriate as the standard sample. FIG. 16 shows a relation between the hardness obtained by a Vickers test and the hardness obtained by substituting the reference function of the equation (6) according to this invention for the indenting force of 445 $\mu N$. With respect to the standard curve for the single crystals as the single material, practical steels have increased hardness by the Vickers test with the reasons as described above. It is clearly shown that the single material such as single crystals is preferred as the standard sample.

INDUSTRIAL APPLICABILITY

According to the invention of this application, as has been explained specifically above, the hardness of the micro region can be evaluated accurately.

In the study directed to the nanometer region, since observing equipment such as TEM, analyzers such as AES and AP are utilized, the micro hardness test of this invention can contribute to the development of materials in cooperation with the apparatus described above as the means for evaluating the mechanical properties.

Further, also with a practical point of view, the hardness evaluation method is used in various fields and progress in the research and development can be expected, and it can improve the reliability and the production efficiency when utilized as the quality control means in actual production sites.

What is claimed is:

1. A testing method for determining the hardness of a micro region. using indentation curves indicating relations between observed penetration depths and indenting forces when an arbitrary shaped indenter is pushed into standard samples of plural types, comprising:

(1) measuring relations between observed penetration depths and indenting forces when the arbitrary shaped indenter is pushed into standard samples of plural types, to prepare the indentation curves, (2) determining a reference function indicative of macro hardness, by standardizing the relations between the indenting forces and macro hardness at the same penetration depth as an index, for the indentation curves of the standard samples of plural types, (3) measuring a relation between the penetration depth and indenting force of an arbitrary sample, and (4) determining the hardness of a micro region from the measured value in step (3) according to the reference function as determined in step (2).

2. The method according to claim 1, wherein each standard sample of plural types has an identical mechanical property in the micrometer region and the nanometer region.

3. A method for determining the hardness of a micro region of a test sample, which comprises:

providing a plurality of different standard samples, contacting each standard sample with an indenter at a plurality of different indenting forces, to thereby cause the indenter to penetrate each standard sample at different penetration depths, measuring the penetration depth formed in each standard sample under each indenting force, determining a relationship between the penetrating depths and indenting forces for each standard sample, determining a standardized relationship between indenting force and macro hardness for the plurality of different standard samples using the same penetration depth as an index, determining a reference function between indenting force, macro hardness and penetration depth for an arbitrary test sample, contacting the test sample with the indenter at an indenting force, and measuring the penetration depth formed in the test sample under the indenting force, determining the hardness of the micro region of the test sample using the reference function.

4. The method according to claim 3, wherein the step of determining the relationship between the penetrating depths and indenting forces for each standard sample includes a step of preparing indentation curves for each standard sample.

5. The method according to claim 3, wherein the plurality of different standard samples are selected from iron, nickel, molybdenum and tungsten.

6. The method according to claim 3, wherein the standard samples are single crystals.

7. The method according to claim 3, wherein the standard samples have electrolytically polished surfaces or buffed polished surfaces.

8. The method according to claim 3, wherein the indenter is a diamond pyramidal indenter.

9. The method according to claim 3, wherein the indenter has an apex of 60° or 115°.

10. The method according to claim 3, wherein each different standard sample has an identical mechanical property in the micrometer region and in the nanometer region.

* * * * *